United States Patent
McKee et al.

(10) Patent No.: US 10,732,145 B2
(45) Date of Patent: Aug. 4, 2020

(54) ELECTROPHORESIS RECEPTACLES AND METHODS

(71) Applicant: Bio-Rad Laboratories, Inc., Hercules, CA (US)

(72) Inventors: Clayton McKee, Hercules, CA (US); Cory Panattoni, Hercules, CA (US); Paul Liu, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 126 days.

(21) Appl. No.: 15/758,445

(22) PCT Filed: Sep. 22, 2016

(86) PCT No.: PCT/US2016/053047
§ 371 (c)(1),
(2) Date: Mar. 8, 2018

(87) PCT Pub. No.: WO2017/053531
PCT Pub. Date: Mar. 30, 2017

(65) Prior Publication Data
US 2018/0252676 A1    Sep. 6, 2018

Related U.S. Application Data

(60) Provisional application No. 62/222,039, filed on Sep. 22, 2015.

(51) Int. Cl.
*G01N 27/447* (2006.01)
*G01N 33/68* (2006.01)

(52) U.S. Cl.
CPC ... *G01N 27/44747* (2013.01); *G01N 27/4473* (2013.01); *G01N 27/44704* (2013.01);
(Continued)

(58) Field of Classification Search
CPC ......... G01N 27/44747; G01N 27/4473; G01N 27/44743; G01N 27/44782; G01N 33/6803; G01N 27/44704
See application file for complete search history.

(56) References Cited

U.S. PATENT DOCUMENTS

| | | | |
|---|---|---|---|
| 3,491,883 A | 1/1970 | Schriftman | |
| 5,411,657 A | 5/1995 | Leka | |

(Continued)

FOREIGN PATENT DOCUMENTS

| | | |
|---|---|---|
| CN | 104335034 A | 2/2015 |
| WO | 2013/180637 A1 | 12/2013 |

OTHER PUBLICATIONS

C. Li, et al. ("Isoelectric focusing in cyclic olefin copolymer microfluidic channels coated by polyacrylamide using a UV photografting method", Electrophoresis, 26(9): p. 1800-1806, May 2005.*
(Continued)

*Primary Examiner* — J. Christopher Ball
(74) *Attorney, Agent, or Firm* — Kilpatrick Townsend and Stockton LLP

(57) ABSTRACT

Gel electrophoresis receptacles and methods of using such receptacles are provided. In one embodiment, a receptacle comprises a cavity for receiving an electrophoresis gel, wherein at least a portion of the receptacle is formed from cyclic olefin copolymer or cyclic olefin polymer.

16 Claims, 4 Drawing Sheets

(52) U.S. Cl.
CPC . *G01N 27/44743* (2013.01); *G01N 27/44782* (2013.01); *G01N 33/6803* (2013.01)

(56) References Cited

U.S. PATENT DOCUMENTS

| | | | |
|---|---|---|---|
| 6,203,679 | B1 | 3/2001 | Bouis et al. |
| 6,290,831 | B1 | 9/2001 | Liran et al. |
| 6,787,016 | B2 | 9/2004 | Tan et al. |
| 6,951,898 | B2 | 10/2005 | Hammond et al. |
| 7,588,673 | B2 | 9/2009 | Latham |
| 8,007,646 | B2 | 8/2011 | Edwards et al. |
| 8,609,423 | B2 | 12/2013 | Diller et al. |
| 2004/0134784 | A1 | 7/2004 | Panattoni et al. |
| 2005/0287618 | A1 | 12/2005 | Haugland et al. |
| 2009/0020427 | A1 | 1/2009 | Tan et al. |
| 2009/0145759 | A1 | 6/2009 | Margalit |
| 2010/0089753 | A1 | 4/2010 | Edwards et al. |
| 2013/0020199 | A1 | 1/2013 | Margalit |
| 2013/0121892 | A1 | 5/2013 | Fuhrmann et al. |
| 2014/0138248 | A1 | 5/2014 | McKee et al. |
| 2014/0234979 | A1 | 8/2014 | Diller et al. |

OTHER PUBLICATIONS

International Search Report and Written Opinion in PCT/US2016/053047; dated Dec. 20, 2016; 15 pages.
Invitrogen life technologies, "LumioTM Technology" brochure, printed 2004, pp. 1-12.
Bio-Rad Laboratories, Inc. Electrophoresis and Blotting Catalog, "Nucleic Acid Electrophoresis and Blotting," 2013, pp. 224-226.
Life Technologies E-Page™ Technical Guide, "Visualizing Lumio™ Fusion Proteins" Publication Part No. 25-0644, Revision Date: Dec. 9, 2012, p. 44.
Extended European Search Report in EP Application 16849574.5 dated May 9, 2019; 8 pages.

\* cited by examiner

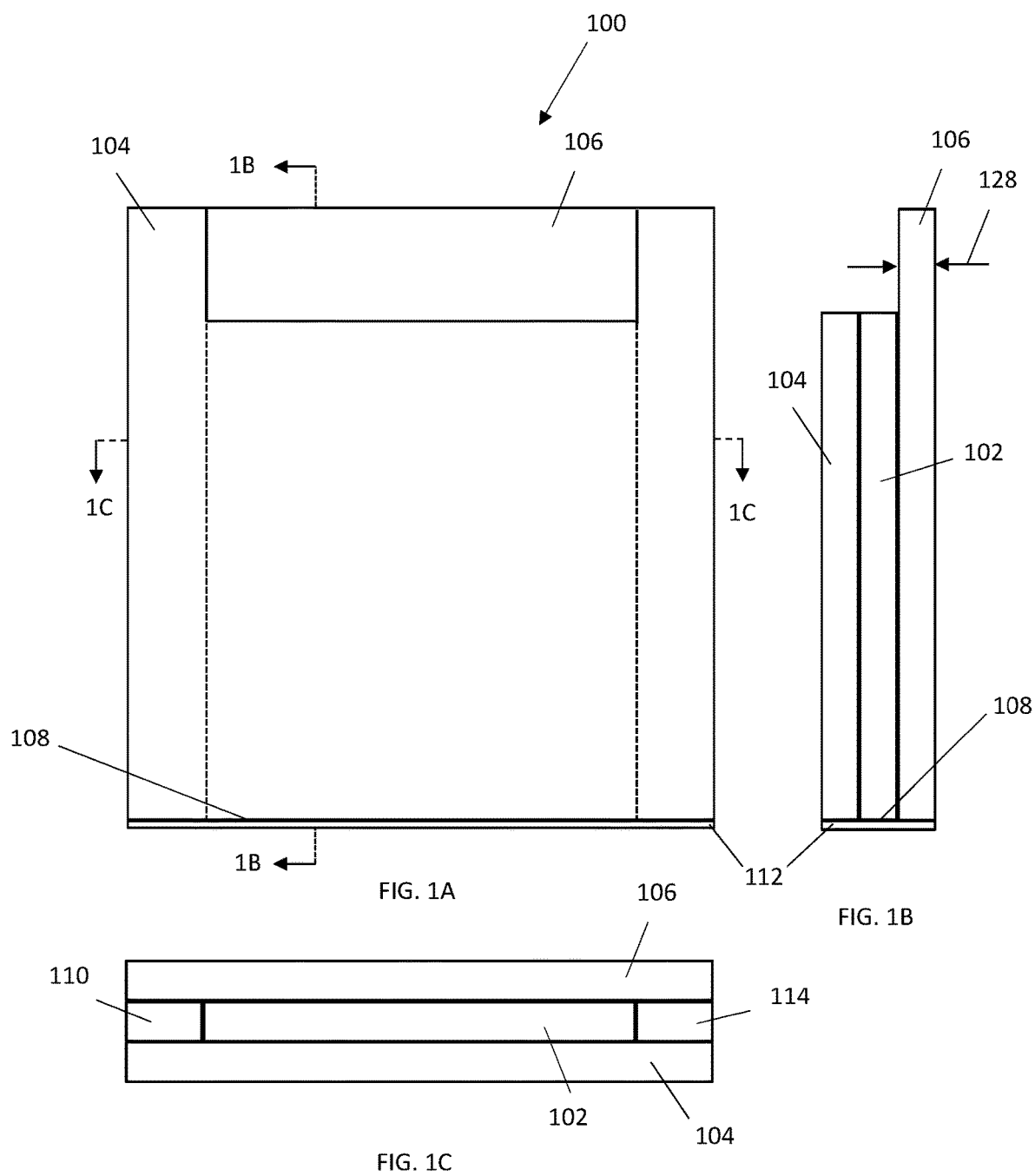

ELECTROPHORESIS RECEPTACLES AND METHODS

CROSS-REFERENCE TO RELATED APPLICATIONS

This application is a U.S. National Phase application under 35 U.S.C. § 371 of International Application No. PCT/US2016/053047, filed Sep. 22, 2016, which claims priority to U.S. Provisional Application No. 62/222,039, filed Sep. 22, 2015, each of which is incorporated by reference herein in its entirety for all purposes.

BACKGROUND

Gel electrophoresis is commonly used to separate and analyze biological substances such as proteins and nucleic acids. In gel electrophoresis, a polyacrylamide or agarose gel in a tube or sandwiched as a slab between glass or plastic plates is placed in an apparatus in which an electric potential is applied to the gel, causing the biological substances to travel through the gel. As the substances travel through the gel, they separate from each other based on size, charge density, and/or conformation to form bands.

After electrophoresis, the cassette plates are typically removed prior to staining and/or visualizing pre-labeled bands in the gel with an ultraviolet-activated or excited dye because the plate material can block ultraviolet light.

SUMMARY

Disclosed herein are receptacles and methods of using such receptacles for gel electrophoresis and subsequent visualization.

In an embodiment, a receptacle includes a cavity for receiving an electrophoresis gel, wherein at least a portion of the receptacle is formed from cyclic olefin copolymer or cyclic olefin polymer. In some embodiments, the receptacle includes an electrophoresis gel which has a label incorporated therein. In some embodiments, the label is a haloalkane selected from the group consisting of trichloroethanol, chloroform, trichloroacetic acid, trichloroethane, bromoform, and iodoacetic acid. In certain embodiments, the label is a UV excitable dye selected from the group consisting of Alexa Fluor 350, Pacific Orange™ dye, Cascade® Blue, Cascade Yellow, dansyl chloride, dapoxyl dye, and bimane. In some embodiments, the label is ethidium bromide. In some embodiments, the receptacle comprises a first support and a second support joined by a liquid-tight seal running continuously or semi-continuously along a first side edge, a bottom edge and a second side edge of the receptacle. In some embodiments, a thickness of at least one of the first and second supports ranges from 0.1 millimeters to 2.0 millimeters. In certain embodiments, a thickness of at least one of the first and second supports ranges from 1.0 millimeter to 2.0 millimeters. In some embodiments, a thickness of at least one of the first and second supports ranges from 0.1 millimeters to 1.0 millimeter. In certain embodiments, the first support and/or the second support comprise(s) a barrier coating on a gel-facing surface. In some embodiments, the barrier coating is polyvinylidene chloride copolymer emulsion or polychlorotrifluoroethylene.

In some embodiments, the receptacle is a tray having a planar base and two opposing walls. In some embodiments, a thickness of the planar base ranges from 0.1 millimeters to 2.0 millimeters. In certain embodiments, a thickness of the planar base ranges from 1.0 millimeter to 2.0 millimeters. In some embodiments, a thickness of the planar base ranges from 0.1 millimeters to 1.0 millimeter.

In an embodiment, a method includes providing a receptacle comprising: an electrophoresis gel having a substance separated therein, wherein the substance comprises a label capable of emitting a signal when illuminated with ultraviolet light; and a cavity for receiving the electrophoresis gel, wherein at least a portion of the receptacle is formed of cyclic olefin copolymer or cyclic olefin polymer; illuminating the receptacle with ultraviolet light; and detecting the signal emitted from the label without removing the electrophoresis gel from the receptacle. In some embodiments, the substance is labeled with the label before or during separation in the electrophoresis gel.

BRIEF DESCRIPTION OF THE DRAWINGS

FIGS. 1A-1C show top and cross sectional views of a receptacle (e.g., a cassette) according to an embodiment of the invention.

DETAILED DESCRIPTION

Figure 2A:
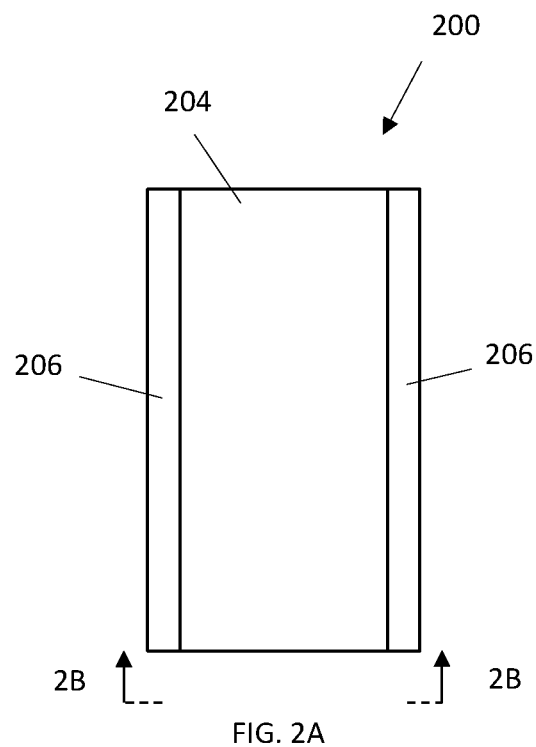
FIGS. 2A and 2B show top and side views of a receptacle (e.g., a tray) according to an embodiment of the invention.

Described herein are receptacles and methods for gel electrophoresis. Receptacles and methods have been discovered in which an ultraviolet-activated or excited signal from a labeled substance in the gel can be detected without removing the gel from the receptacle.

Definitions

Unless defined otherwise, technical and scientific terms used herein have the same meaning as commonly understood by a person of ordinary skill in the art. The terms "a", "an", and "the" are intended to mean "one or more." The term "comprise," and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

The term "protein" refers to an amino acid polymer or a set of two or more interacting or bound amino acid polymers. The terms applies to amino acid polymers in which one or more amino acid residue is an artificial chemical mimetic of a corresponding naturally occurring amino acid, as well as to naturally occurring amino acid polymers, those containing modified residues, and non-naturally occurring amino acid polymers.

The term "nucleic acid" refers to deoxyribonucleic acid (DNA), ribonucleic acid (RNA), single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot) or another moiety.

Receptacle

Referring to FIGS. 1A-1C and FIGS. 2A-2B, receptacles 100 and 200, respectively, for gel electrophoresis are illustrated. At least a portion of the receptacles 100 and 200 are formed from a plastic that is transparent to ultraviolet (UV) light. In some embodiments, the plastic is transparent to UV light ranging from 200 nanometers to 400 nanometers. In some embodiments, the plastic is also transparent to visible and/or infra-red light. Exemplary UV transparent plastics include, but are not limited to, cyclic olefin copolymer (e.g., TOPAS® grade 8007, 5013, 6013, 6015 or 6017), cyclic olefin polymer (e.g., ZEON ZEONEX® grade 480, 480R, E48R, F52R, K26R, 330R, or 350R), polystyrene, and/or polymethyl methacrylate. The receptacles 100 and 200 can be formed by injection molding.

In the embodiment illustrated in FIGS. 1A-1C, the receptacle 100 (e.g., a cassette) is generally rectangular in shape and includes a cavity for an electrophoresis gel 102. In some embodiments, the receptacle 100 includes a first support 104 and a second support 106 formed from the plastic that is transparent to UV light. In some embodiments, the first support 104 is formed from plastic that is transparent to UV light and the second support 106 is formed from glass. In some embodiments, the first support 104 is formed from a first plastic that is transparent to UV light and the second support 106 is formed from a second plastic that is not transparent to UV. Exemplary plastics that are not transparent to UV light include, but are not limited to, polycarbonate, and polyethylene terephthalate.

In some embodiments, the first and second supports 104, 106 are joined by a liquid-tight seal 108 running continuously or semi-continuously along a first side edge 110, a bottom edge 112 and a second side edge 114. The liquid-tight seal 108 is used to seal the cavity during gel formation in the assembled receptacle 100. In some embodiments, the liquid-tight seal 108 is one or more spacers along each side edge 110,114 and adhesive tape along the bottom edge 112 of the receptacle 100. In some embodiments, the liquid-tight seal 108 is one or more spacers along the side edges 110,114 and bottom edge 112. In some embodiments, the liquid-tight seal 108 is an embossment or ridge on a gel-facing surface of the first support 104 or the second support 106 running along the side edges 110,114 and bottom edge 112. During assembly of the receptacle 100, the first support 104 can be secured to the second support 106 through the liquid-tight seal 108 (e.g., ridge) by ultrasonic welding. The liquid-tight seal 108 further helps dictate the spacing between the first and second supports 104, 106 when the supports 104, 106 are joined together. In some embodiments, the first support 104, the second support 106 and the liquid-tight seal 108 are fabricated as a single piece of plastic.

In some embodiments, the cavity formed by the first support 104, the second support 106 and the liquid-tight seal 108 is capable of containing and confining gel material that can form a gel between 0.5 millimeters and 1.5 millimeters thick. The gel can be formed by manually or automatically adding gel material to the chamber from an opening 115 in the cassette 100.

In some embodiments, a gel-facing surface of each of the first and second supports 104, 106 is coated with a barrier coating (e.g., an oxygen impermeable substance) and/or a release agent (e.g, a hydrophilic polymer). In certain embodiments, the gel-facing surface of each support is treated with a barrier coating that blocks oxygen. Oxygen interferes with polyacrylamide gel polymerization, as described in U.S. patent application Ser. No. 14/085,472, which is incorporated by reference in its entirety herein. In some embodiments, the gel-facing surface of each support is treated with polyvinylidene chloride, low-density polyethylene and/or acrylonitrile methyl acetate copolymer. In some embodiments, the barrier coating is polyvinylidene chloride copolymer emulsion (e.g., Serfene™ 411 and/or Serfene™ 2060 from Dow). In certain embodiments, the barrier coating is polychlorotrifluoroethylene (e.g., Aclar® from Honeywell). In some embodiments, the gel-facing surface of each support is coated with a release agent including, but not limited to, polyvinyl acetate, polyethylene glycol and/or starch. Exemplary techniques for applying a barrier coating and/or release agent to one or more surfaces of the sheets include, but are not limited to, spraying, dipping, painting or spin coating.

Each of the supports 104, 106 is thin enough to allow UV light to pass through while providing sufficient stiffness to limit deflection of the supports during gel formation and use. In some embodiments, a thickness 128 of at least one of the supports 104, 106 ranges from 0.1 millimeters to 2.0 millimeters, 1.0 millimeter to 2.0 millimeters, or 0.1 millimeters to 1.0 millimeter.

The receptacle 100 and gel 102 housed in the receptacle 100 can be any suitable width or length. In some embodiments, the receptacles are 10 centimeters to 15 centimeters in width by 8 centimeters to 11 centimeters in length. In some embodiments, the gel housed in the receptacle is 7 centimeters to 9 centimeters in length (i.e., running length) by 9 centimeters to 13 centimeters wide.

The receptacle 100 can be provided with or without an electrophoresis gel 102. In embodiments in which the receptacle 100 is provided with an electrophoresis gel 102, the electrophoresis gel 102 can also be provided with pre-formed wells for loading substances (e.g., proteins or nucleic acids) to be separated in the gel. In embodiments in which the receptacle 100 is used to separate proteins, the electrophoresis gel 102 can be provided with a stacking gel with pre-formed wells. Exemplary materials from which the electrophoresis gel 102 can be formed include polyacrylamide and agarose. In embodiments in which the gel 102 comprises polyacrylamide, the polyacrylamide can be present at any percentage or concentration, including at more than one concentration (e.g., in stacking and resolving portions of the gel) or at a gradient of concentrations. The polyacrylamide gel can also comprise a denaturing agent such as sodium dodecyl sulfate, as well as a buffering agent including, but not limited to, tris(hydroxymethyl)aminomethane (Tris), or tricine. In embodiments in which the electrophoresis gel 102 comprises agarose, the agarose can be present at any percentage or concentration. The agarose gel can also include a buffering agent including, but not limited to, Tris-acetate with ethylenediaminetetraacetic acid (EDTA) or Tris-borate with EDTA.

Figure 2B:
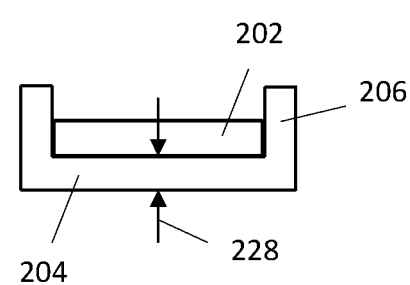

In the embodiment illustrated in FIGS. 2A-2B, the receptacle 200 (e.g., a tray) is generally rectangular in shape and includes a cavity for an electrophoresis gel 202 (e.g., an agarose gel). In some embodiments, the receptacle 200 includes a base 204 and two opposing walls 206 formed from the plastic that is transparent to UV light.

The base 204 of the receptacle 200 is thin enough to allow UV light to pass through while providing sufficient stiffness to limit deflection of the receptacle during gel formation and use. In some embodiments, a thickness 228 of the base 204 ranges from 0.1 millimeters to 2.0 millimeters, 1.0 millimeter to 2.0 millimeters, or 0.1 millimeters to 1.0 millimeter.

The receptacle 200 and gel 202 housed in the receptacle 200 can be any suitable width or length. In some embodiments, the receptacles are 7 centimeters to 16 centimeters by 7 centimeters to 20 centimeters in size.

The receptacle 200 can be provided with or without an electrophoresis gel 202. In embodiments in which the receptacle 200 is provided with an electrophoresis gel 202, the electrophoresis gel 202 can also be provided with preformed wells for loading substances (e.g., nucleic acids) to be separated in the gel. The agarose gel can be present at any percentage or concentration. The agarose gel can also include a buffering agent including, but not limited to, Tris-acetate with ethylenediaminetetraacetic acid (EDTA) or Tris-borate with EDTA.

Methods

Figure 3:
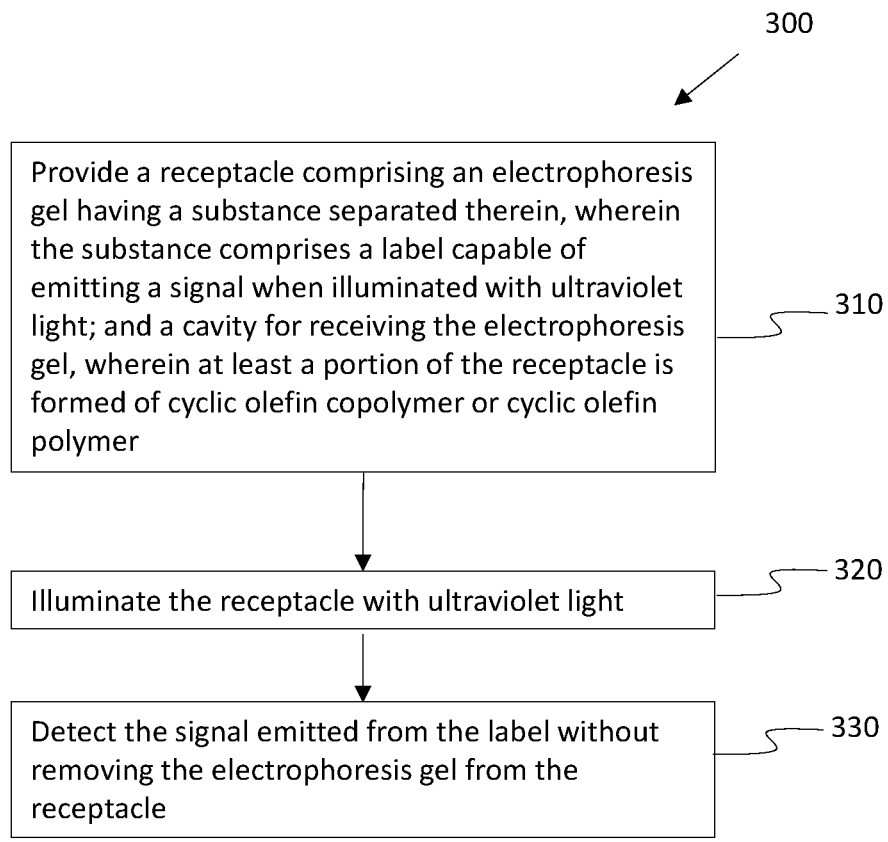
FIG. 3 is a flow chart showing a method according to an embodiment of the invention.

Referring to FIG. 3, a method 300 that uses the aforementioned receptacle 100 or 200 will now be described.

In exemplary step 310, a receptacle 100 or 200 is provided. The receptacle 100 or 200 includes an electrophoresis gel 102 or 202 having a substance separated therein. The receptacle 100 or 200 further includes a cavity for the electrophoresis gel 102 or 202. At least a portion of the receptacle 100 or 200 is formed of a plastic which is transparent to ultraviolet (UV) light.

In methods using receptacle 100, the substance can be a protein or nucleic acid from a sample. In methods using receptacle 200, the substance can be a nucleic acid from a sample. Exemplary samples include, but are not limited to whole blood, plasma, serum, saliva, urine, milk, eggs, ascites, hybridoma supernatant, cell lysate, tissue or cell culture supernatant, and/or water. The substance comprises a label capable of emitting a signal when illuminated with UV light. In some embodiments, the substance is labeled with the label prior to electrophoresis. In certain embodiments, the substance is labeled with the label during electrophoresis.

In some embodiments, the label is activated by UV light. In some embodiments in which proteins are separated in the electrophoresis gel 102, the UV light-activated label is a haloalkane (i.e., a halo-substituted organic compound) as described in U.S. Pat. Nos. 7,569,103 8,007,646, each of which is incorporated by reference in its entirely. Exemplary haloalkanes include, but are not limited to, trichloroethanol, chloroform, trichloroacetic acid, trichloroethane, bromoform, and iodoacetic acid. The haloalkane can be mixed with the proteins prior to separation in the gel 102, can be included in either or both electrode buffers or can be included in the gel material during gel casting. Methods in which haloalkane is included in either or both electrode buffers are described in U.S. Pat. No. 9,005,418, which is incorporated by reference in its entirely.

In some embodiments in which proteins are separated in the electrophoresis gel 102, the label is excited by UV light. In some embodiments in which proteins are separated in the gel 102, the UV-excitable label includes, but is not limited to, Alexa Fluor 350 and other coumarin derivatives, Pacific Orange™ dye, Cascade® Blue and other pyrene derivatives, Cascade Yellow and other pyridyloxazole derivatives, dansyl chloride, dapoxyl dye, and bimane. In embodiments in which the UV-excitable label is insoluble or only sparingly soluble in water, the protein can be labeled with the UV-excitable label prior to being separated in the gel by methods as described in U.S. Pat. Nos. 6,995,023 and 7,435,603, each of which is incorporated herein by reference in its entirety.

In some embodiments in which nucleic acids are separated in the electrophoresis gel 102 or 202, the label excited by UV light is ethidium bromide.

Substances in the electrophoresis gel 102 or 202 can be separated by using any techniques desired, and using any available materials or apparatus. In standard practice, the gel 102 or 202 is contacted with an electrolyte-containing buffer and placed between two electrodes, and a current is applied between the electrodes. Electrophoresis causes substances in a sample to migrate within the gel and become separated from each other according to molecular weight, size, or charge. For convenience and if desired, a molecular weight marker can be loaded into the gel 102 or 202 along with the sample, allowing the practitioner to track the positions of substances in the sample during or after migration.

After electrophoresis, the receptacle 100 or 200 is placed in an imager or on a light box without removing the gel from the receptacle 100 or 200. In exemplary step 320, the receptacle 100 or 200 is illuminated with UV light at an appropriate wavelength (e.g., 200 nm-400 nm). The receptacle 100 or 200 can be illuminated by trans-illumination (e.g., from below) or by epi-illumination (e.g., from above). The receptacle 100 can be illuminated through either support. In some embodiments, the separation of the substances in the gel is monitored during electrophoresis and while the receptacle 100 or 200 is illuminated with UV light. Upon illumination, the labels on/in the substances separated within the gel emit a signal (e.g., a fluorescent signal).

In embodiments in which proteins in the gel are labeled with haloalkane, upon exposure to UV light, the haloalkane reacts with the tryptophan residues of the proteins to form "stain-free" haloalkylated tryptophan-containing proteins. The resulting haloalkylated tryptophan residues emit a fluorescent signal. The intensity and duration of UV light exposure are sufficient to cause the reaction to occur and to produce a fluorescent emission that can be detected and quantified. In some embodiments, exposure times from thirty seconds to thirty minutes will provide adequate results. Haloalkane is preferably used to label proteins in the absence of any protein stains so that the procedure is truly stain-free. As used herein, "protein stains" refers to compounds that are color-bearing or fluorescent on their own, i.e., in the absence of any reaction with amino acid residues, and that adhere to proteins by means other than a coupling reaction. Examples of such stains include, but are not limited to, COOMASSIE™ Brilliant Blue, Ponceau S, and SYPRO RUBY™.

In exemplary step 330, the signal emitted from the label is detected or visualized without removing the gel from the receptacle 100 or 200. In some embodiments, detection is achieved by imaging such as by photography or by electronic detectors. Exemplary detectors include, but are not limited to, a camera, a charge coupled device (CCD), a complimentary metal-oxide-semiconductor (CMOS), one or more individual photodiodes, or photodiode arrays. Digital results can be analyzed by conventional imaging software. In embodiments in which haloalkane labeled proteins are detected, the amount of protein in the sample can be quantified or normalized by methods as described in U.S.

patent application 2013/0288388, which is incorporated herein by reference in its entirety.

EXAMPLE

This example demonstrates detection of UV-activated labeled proteins in a denaturing polyacrylamide gel without opening a cassette formed from cyclic olefin copolymer.

Two supports for making a cassette were injection molded from TOPAS cyclic olefin copolymer grade 8007×10. Each support was approximately 10 cm wide by 8 cm long. The thickness of each of the supports was 1.6 mm. The two COC supports were ultrasonically welded together along each side edge to form a cavity for a 1 mm thick polyacrylamide gel. The bottom edge was sealed with adhesive tape.

Figure 4:
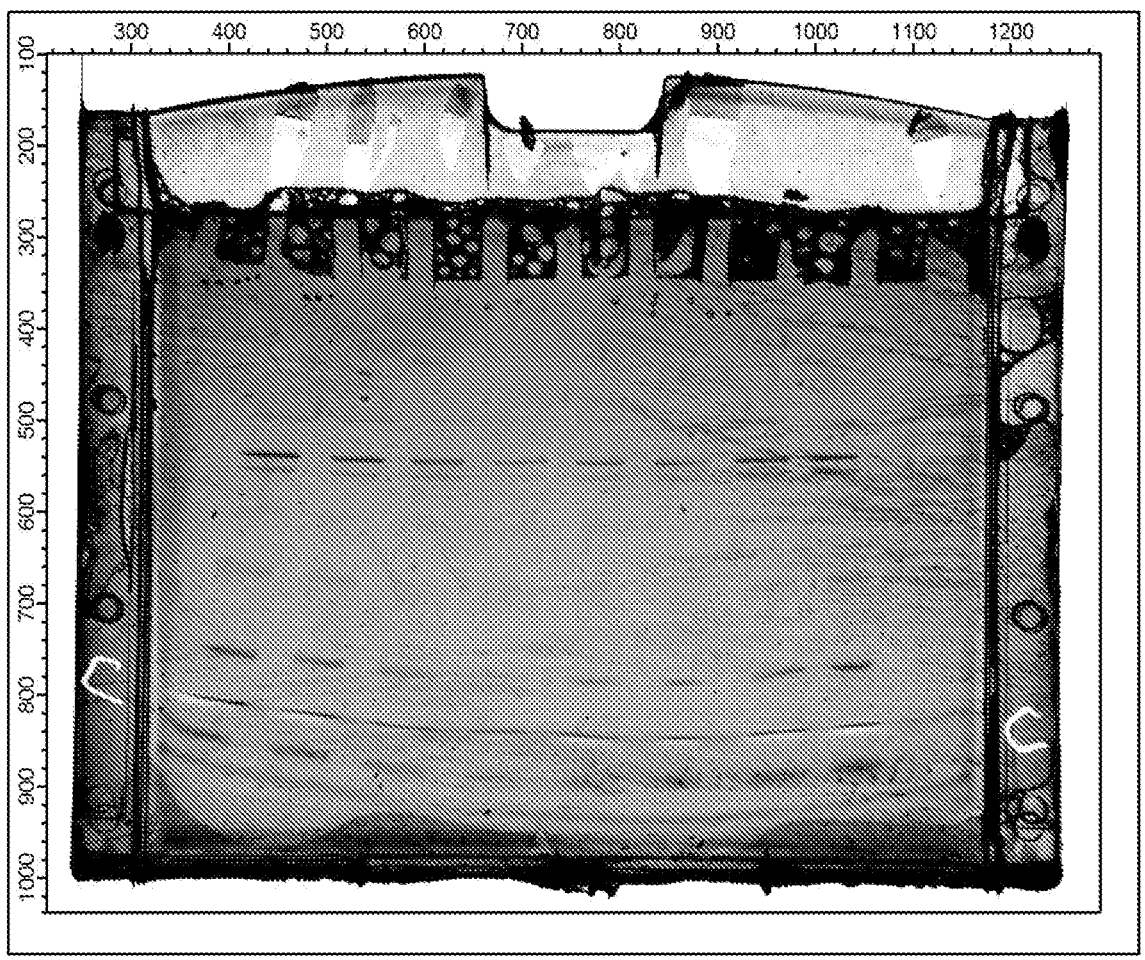
FIG. 4 is an image of a polyacrylamide gel inside a cassette. Haloalkylated tryptophan fluorescence was detected from haloalkane labeled proteins separated in the polyacrylamide gel.

Using the resulting empty cassette, a denaturing 12% polyacrylamide resolving gel/4% stacking gel with 0.5% m/v 2,2,2, trichloroethanol was cast with a ten well comb. A standard gel casting protocol was used. The adhesive tape along the bottom edge of the cassette with the cast gel was removed and the cassette was placed in a Bio-Rad Mini-PROTEAN® Tetra Vertical Electrophoresis Cell. Unstained broad-range SDS-PAGE standards (Bio-Rad Cat. No. 161-0317) were prepared and used as per manufacturer's instructions. After loading the standards into lanes 2-8 of the gel, the standards were electrophoresed at 250V until tracking dye reached the bottom of the gel. After electrophoresis, the cassette was imaged with a ChemiDoc MP system. Without removing the gel from the cassette, the trichloroethanol was reacted with the tryptophan residues in the proteins separated in the gel by exposing the cassette to UV light for 2 minutes. The cassette was then imaged with UV light for 2 seconds. The resulting image in FIG. 4 shows protein bands visible through the cassette supports, illustrating that electrophoretically separated proteins labeled with UV activated labels can be detected in a polyacrylamide gel without removing the gel from a cassette formed from cyclic olefin copolymer.

All patents, patent applications, and other published reference materials cited in this specification are hereby incorporated herein by reference in their entirety.

What is claimed is:

1. A receptacle comprising:
   a first support and a second support joined by a liquid-tight seal running continuously or semi-continuously along a first side edge, a bottom edge and a second side edge of the receptacle, and
   a cavity for receiving an electrophoresis gel,
   wherein at least a portion of the first support and at least a portion of the second support are formed from cyclic olefin copolymer or cyclic olefin polymer, and
   wherein the first support or the second support comprises a barrier coating on a gel-facing surface.

2. The receptacle of claim 1, wherein the receptacle includes an electrophoresis gel having a label incorporated therein.

3. The receptacle of claim 2, wherein the label is a haloalkane selected from the group consisting of trichloroethanol, chloroform, trichloroacetic acid, trichloroethane, bromoform, and iodoacetic acid; or a UV excitable dye.

4. The receptacle of claim 2, wherein the label is ethidium bromide.

5. The receptacle of claim 4 comprising a tray having a planar base and two opposing walls.

6. The receptacle of claim 5, wherein a thickness of the planar base ranges from 0.1 millimeters to 2.0 millimeters.

7. The receptacle of claim 1, wherein a thickness of at least one of the first and second supports ranges from 0.1 millimeters to 2.0 millimeters.

8. The receptacle of claim 1, wherein the barrier coating is polyvinylidene chloride copolymer emulsion or polychlorotrifluoroethylene.

9. A method comprising:
   providing a receptacle comprising:
      an electrophoresis gel having a substance separated therein, wherein the substance comprises a label capable of emitting a signal when illuminated with ultraviolet light;
      a first support and a second support joined by a liquid-tight seal running continuously or semi-continuously along a first side edge, a bottom edge and a second side edge of the receptacle; and
      a cavity for receiving the electrophoresis gel, wherein at least a portion of the first support and at least a portion of the second support are formed of cyclic olefin copolymer or cyclic olefin polymer, and wherein the first support or the second support comprises a barrier coating on a gel-facing surface;
   illuminating the receptacle with ultraviolet light; and
   detecting the signal emitted from the label without removing the electrophoresis gel from the receptacle.

10. The method of claim 9, wherein the substance is labeled with the label before or during separation in the gel electrophoresis.

11. The method of claim 9, wherein the substance is a protein and the label is a haloalkane selected from the group consisting of trichloroethanol, chloroform, trichloroacetic acid, trichloroethane, bromoform, and iodoacetic acid; or a UV excitable dye.

12. The method of claim 9, wherein the substance is a nucleic acid and the label is ethidium bromide.

13. The method of claim 9, wherein a thickness of a wall of at least one of the first and second supports ranges from 0.1 millimeters to 2.0 millimeters.

14. The method of claim 9, wherein the barrier coating is polyvinylidene chloride copolymer emulsion or polychlorotrifluoroethylene.

15. The method of claim 9, wherein the receptacle comprises a tray having a planar base and two opposing walls.

16. The method of claim 15, wherein a thickness of the planar base ranges from 0.1 millimeters to 2.0 millimeters.

* * * * *